United States Patent [19]

Johnson et al.

[11] 4,381,168
[45] Apr. 26, 1983

[54] METHOD AND APPARATUS FOR SEPARATING A LAYER OF FLEXIBLE MATERIAL FROM A SURFACE

[75] Inventors: Wayne S. Johnson, La Habra; Vincent C. Tangherlini, Costa Mesa, both of Calif.

[73] Assignee: Beckman Instruments, Inc., Fullerton, Calif.

[21] Appl. No.: 225,830

[22] Filed: Jan. 16, 1981

[51] Int. Cl.³ .................. B65H 29/08; B29C 7/00
[52] U.S. Cl. .................. 414/737; 264/335; 271/95; 414/786
[58] Field of Search ........... 414/121, 590, 737, 786; 271/95, 107; 264/334, 335; 425/554, 556, 584

[56] References Cited

U.S. PATENT DOCUMENTS

| | | | |
|---|---|---|---|
| 2,973,610 | 3/1961 | Randall | 271/107 X |
| 2,995,360 | 8/1961 | Simpson | 271/107 |
| 3,176,976 | 4/1965 | Hepp | 271/95 X |
| 3,327,029 | 6/1967 | Pincus et al. | 264/335 X |
| 3,599,970 | 8/1971 | Smithe et al. | 271/95 |
| 3,767,560 | 10/1973 | Elevitch | 204/299 |

Primary Examiner—Leslie J. Paperner
Attorney, Agent, or Firm—R. J. Steinmeyer; J. E. Vanderburgh; Timothy R. Schulte

[57] ABSTRACT

A method and apparatus for removing a flexible layer from a substantially flat mold or other surface. A curvilinear removal head, including a vacuum manifold holding one end of the flexible layer, pivots to peel the flexible layer from the mold.

2 Claims, 3 Drawing Figures

METHOD AND APPARATUS FOR SEPARATING A LAYER OF FLEXIBLE MATERIAL FROM A SURFACE

BACKGROUND OF THE INVENTION

1. Field of the Invention

The invention relates to the field of removal devices. More particularly, the invention relates to the field of removal heads where a flexible layer of material is removed from a mold or other container. By way of further characterization, but not by way of limitation thereto, the invention is a curvilinear removal head which includes a vacuum source to contact one edge of a flexible sheet such that rotation of the removal head peels the flexible material from a mold.

2. Description of the Prior Art

The manufacture and molding of relatively thin, flexible layers of materials such as agarose gels for electrophoresis has traditionally been a manual, time consuming, procedure. Relatively recent automation of this process has reduced the time and personnel required to mold these materials. However, automated procedures present special problems. One of these problems is the removal of the cast gel layer from the mold without damaging the gel layer. In manual systems the removal of the gel layer was done with tweezers or other means to peel or strip the gel layer from the mold. For automated systems it is desirable to have a device which can remove the gel layer from the mold quickly and without any damage to the gel layer.

Prior automated gel casting apparatus, such as that shown in U.S. Pat. No. 3,635,808 issued to F. R. Elevitch on Jan. 18, 1972, emphasized the use of release agents in the molds to prevent the gel from adhering to the mold. In this device the mold is lowered onto a continuous strip of backing material and the agarose gel is injected into the mold. The mold is then tilted to peel it from the cast gel layer. While suited for its intended purpose, this device can result in damage to the gel layer. In addition, this device requires multiple movements of the mold which may not be practical.

Another device, which is shown in U.S. Pat. No. 3,767,560 issued to F. R. Elevitch on Oct. 23, 1973 (a division of the above referenced patent), uses continuous rolling molds. That is, the individual molds are contained on a roll. A continuous layer of backing material with the gel solution thereon is passed below the roll of molds. The gel layers formed thereby are peeled from the molds by the rotating action of the molds in combination with the movement of the backing material on a continuous belt. While suited for its intended purpose, this device does not allow for the flat molding of the gels. That is, the gels are molded on a curved surface which may result in nonuniformity of, and damage to, the gel layer when it is placed on a flat surface.

SUMMARY OF THE INVENTION

The invention is a method and apparatus for removing a layer of flexible material from a substantially flat surface. A curvilinear removal head is movable with respect to the surface. A holding means is cooperative with the curvilinear face to contact a portion of the flexible material.

In the preferred embodiment the removal head is a cylindrical segment. The holding means includes a vacuum manifold which is movably mounted on the curvilinear face of the removal head. The flexible material includes a backing sheet with a gel layer adherent thereto. The vacuum manifold is brought into contact with a portion of the backing sheet. Rotation of the removal head coupled with lateral movement of the removal head with respect to the mold results in the peeling of the gel from the mold. With the backing sheet and gel hanging from the vacuum manifold, the removal head may be moved to a position where the gel and backing sheet may be placed on a transfer mechanism with the backing sheet down. Therefore, the gel layer may be removed from the mold and placed on another surface without contacting any surface after being removed from the mold. Damage to, or contamination of, the gel surface is thus prevented.

DESCRIPTION OF THE PREFERRED EMBODIMENT

Figure 1:
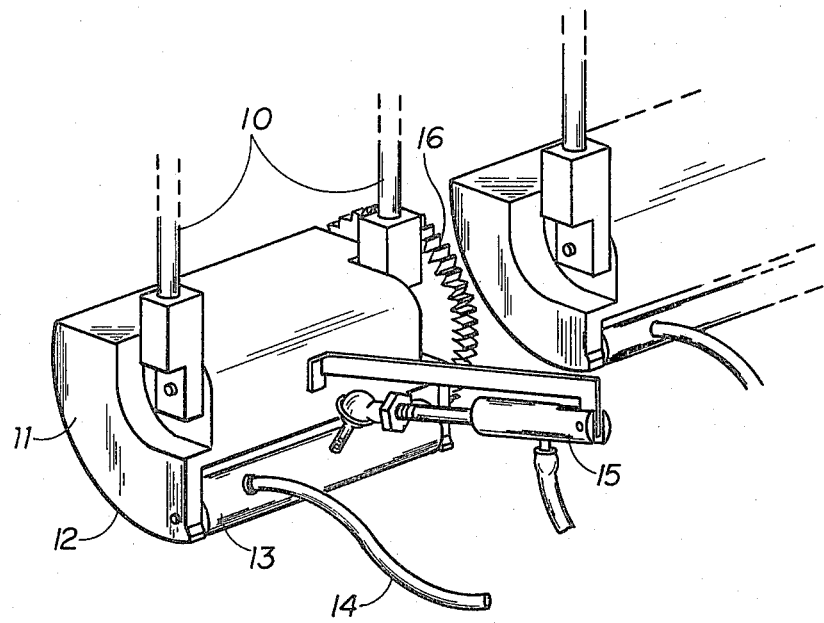
FIG. 1 is a perspective view of the rear of the removal head assembly.

Referring to FIG. 1, a plurality of guide rods 10 support a removal head 11 which includes a curvilinear face 12. A holding means which may include a vacuum manifold 13 is pivotally mounted on removal head 11. A vacuum source (not shown) is connected to vacuum manifold 13 by a hose 14. A conventional pneumatic drive 15 is connected to removal head 11 and vacuum manifold 13 to rotate manifold 13 on a pin or other suitable means in head 11. A gear 16 is connected to removal head 11.

Figure 2:
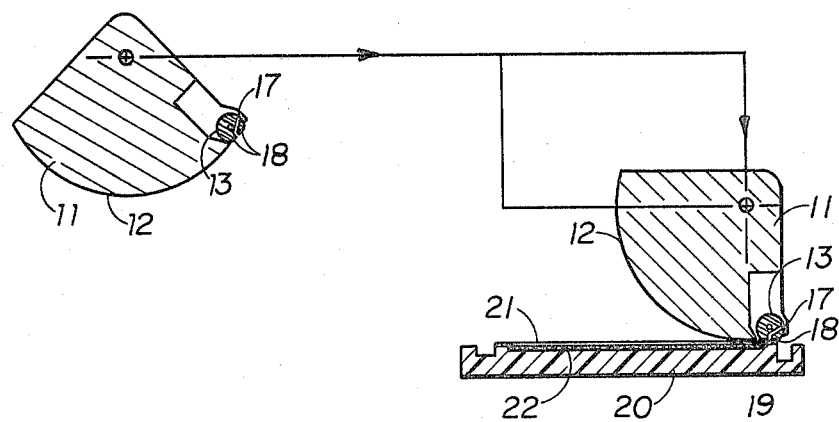
FIG. 2 is a side sectional view of the removal head illustrating its movement and operation in contacting the backing sheet on a mold.

Referring to FIG. 2, removal head 11 is shown in a side sectional view. Vacuum manifold 13 is pivotally mounted on removal head 11. A passage 17 is shown in vacuum manifold 13. While only one passage 17 is shown, it should be expressly understood that a plurality of these passages may be provided along the length of manifold 13. A sealing member which may include a silicone rubber seal 18 is provided on the flat side of manifold 13. The movement sequence for removal head 11 with respect to a mold 20 is illustrated. In one position removal head 11 is shown positioned adjacent mold 20. The flat side of manifold 13 including passage 17 is positioned against an edge 19 of a blocking sheet 21. Backing sheet 21 is in adherent contact with a surface of a gel layer 22. Edge 19 extends beyond the contacted surface of gel layer 22 and rests on mold 20.

Figure 3:
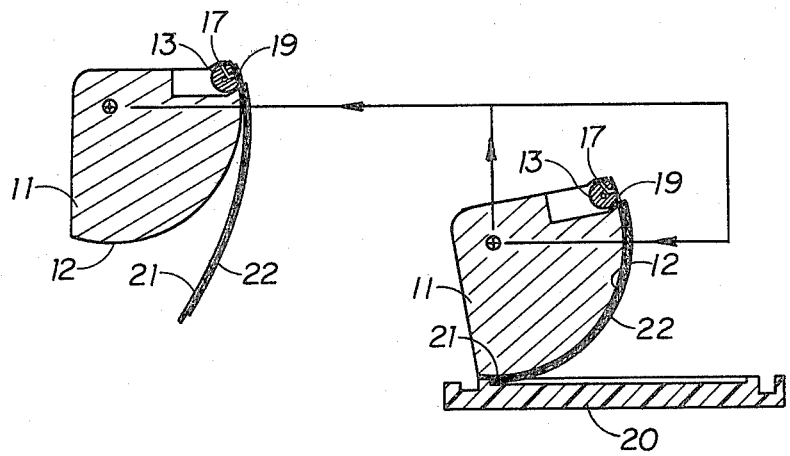
FIG. 3 is a side sectional view of the removal head illustrating its movement after peeling the gel layer from the mold.

Referring to FIG. 3, a side sectional view of removal head 11 is shown illustrating the movement of removal head 11 during and after removal of gel layer 22 from mold 20. That is, once gel layer 22 has been peeled from mold 20 by the pivotal and lateral movement of removal head 11, then removal head 11 is moved up and away from mold 20 to its original location as shown in FIG. 2. Backing sheet 21 is held to vacuum manifold 13 by a vacuum applied through passage 17 to edge 19 of backing sheet 21.

Mode of Operation

Referring to FIGS. 1 and 2, removal head 11 is moved into a position adjacent mold 20. Removal head 11 is moved laterally and up and down by an oilless pneumatic cylinder (not shown) connected to guide rods 10. Removal head 11 is rotated by the interaction of gear 16 with another gear on the apparatus (not shown). While only one gear 16 is shown in FIG. 1, it should be understood that a plurality of removal heads 11 and gears 16 may be utilized in parallel alignment. Once in position adjacent mold 20, vacuum manifold 13 is rotated by conventional pneumatic drive 15 such that passage 17 is sealed against edge 19 by seal 18. As the flat side of vacuum manifold 13 comes in contact with edge 19, downward pressure is applied by removal head 11 to hold edge 19 between vacuum manifold 13 and mold 20. The airtight seal between seal 18 and edge 19 allows a vacuum to be applied through passage 17 to secure edge 19 to vacuum manifold 13.

Referring to FIG. 3, lateral movement of removal head 11 in combination with the rolling movement along curvilinear face 12 of removal head 11 strips gel layer 22 from mold 20 without damage. This removal sequence is shown in FIG. 3. Removal head 11 is then lifted away from mold 18 to the position at the left in FIG. 3. During this movement, backing sheet 21 is held to removal head 11 by the vacuum applied to edge 19 through passage 17 in manifold 13.

In the position shown at the left in FIG. 3, gel layer 22 and backing sheet 21 are ready to be placed on a transfer mechanism (not shown). That is, vacuum manifold 13 may be rotated by pneumatic drive 15 (FIG. 1) and removal head 11 may be lowered to allow the transfer mechanism such as a belt to contact the bottom of backing sheet 21. Rotation of manifold 13 facilitates this positioning movement. Movement of the transfer belt, left to right in FIG. 3, combined with the subsequent release of the vacuum through passage 17, allows backing sheet 21 and gel layer 22 to drop onto the transfer belt with gel layer 22 facing away from the transfer belt. Thus, the removal of gel layer 22 from mold 18 is accomplished without any contact being made with gel layer 22. The absence of relative lateral motion between gel layer 22 and mold 18 during removal due to the rolling action of curvilinear face 12 on removal head 11 prevents tearing or other damage to the surface of gel layer 22. This results in improved quality and more consistent results during electrophoresis using gel layer 22.

While the invention has been disclosed with respect to a particular embodiment thereof, it is not to be so limited as changes and modifications may be made which are within the intended scope of the appended claims. For example, while a vacuum apparatus is used to hold edge 19 to removal head 11, other arrangements could be utilized for this purpose. The invention could be used when any flexible item must be removed from a mold, well, or slot during a manufacturing or handling process. The device is especially useful where such removal must be accomplished without damage to the flexible item and/or where it is desired not to contact the flexible item directly.

The foregoing description, taken together with the appended claims, constitutes a disclosure such as to enable a person skilled in the art and having the benefits of the teachings contained therein to make and use the invention. Further, the structure herein described constitutes a meritorious advance in the art which is unobvious to such skilled workers not having the benefit of these teachings.

What is claimed is:

1. A device for separating a layer of flexible material from a substantially flat surface comprising:
a removal head mounted adjacent said surface for relative movement with respect thereto;
said removal head including a curvilinear face on at least a portion of said removal head;
a vacuum manifold rotatably mounted on said removal head adjacent to said curvilinear face;
means for moving said curved removal head and said flexible material away from said surface;
and whereby, when said removal head is moved away from said surface and said vacuum head is rotated, said layer is separated from said removal head.

2. Method for separating a layer of flexible material from a surface comprising the steps of:
placing a vacuum manifold on which is rotatably mounted a curved removal head in contact with a portion of said flexible material;
holding said portion of said flexible material against said vacuum manifold;
rolling said curved removal head in the direction of a portion of said flexible material which is not held against said vacuum manifold;
moving said curved removal head and said flexible material away from said surface;
rotating said vacuum manifold to separate said flexible material from said curved removal head; and
releasing said portion of said flexible material from said vacuum manifold.

* * * * *